United States Patent
Kopelman

(10) Patent No.: US 8,402,678 B1
(45) Date of Patent: Mar. 26, 2013

(54) ORTHOPEDIC SHOE/BOOT FOR USE WITH FOOT WOUNDS AND FOR POST OP AMBULATION

(75) Inventor: Jeff D. Kopelman, St. Petersburg, FL (US)

(73) Assignee: Jeff Kopelman. L.L.C., St. Petersburg, FL (US)

( * ) Notice: Subject to any disclaimer, the term of this patent is extended or adjusted under 35 U.S.C. 154(b) by 0 days.

(21) Appl. No.: 13/553,343

(22) Filed: Jul. 19, 2012

(51) Int. Cl.
*A61F 5/00* (2006.01)
*A61F 5/052* (2006.01)

(52) U.S. Cl. .................. 36/140; 36/7.5; 36/103; 602/23
(58) Field of Classification Search ...... 36/7.5, 36/110, 140, 103, 102, 100; 602/23, 27, 602/30, 65
See application file for complete search history.

(56) References Cited

U.S. PATENT DOCUMENTS

| | | | | |
|---|---|---|---|---|
| 4,351,324 | A | * | 9/1982 | Bronkhorst ............ 602/27 |
| 4,677,767 | A | | 7/1987 | Darby |
| 4,726,127 | A | | 2/1988 | Barouk |
| 5,020,523 | A | * | 6/1991 | Bodine ............ 602/27 |
| 5,078,128 | A | | 1/1992 | Grim et al. |
| 5,138,777 | A | | 8/1992 | Darby |
| 5,151,081 | A | * | 9/1992 | Williams ............ 602/27 |
| D338,273 | S | * | 8/1993 | Williams ............ D24/192 |
| 5,329,705 | A | | 7/1994 | Grim et al. |
| 5,370,133 | A | * | 12/1994 | Darby et al. ............ 128/882 |
| 5,378,223 | A | | 1/1995 | Grim et al. |
| 5,464,385 | A | | 11/1995 | Grim |
| 5,537,764 | A | | 7/1996 | Prahl |
| 5,566,479 | A | | 10/1996 | Gray et al. |
| 5,761,834 | A | | 6/1998 | Grim et al. |
| 5,797,862 | A | | 8/1998 | Lamont |
| 5,940,992 | A | | 8/1999 | Darby |
| 5,997,491 | A | * | 12/1999 | Harris ............ 602/6 |
| 6,212,798 | B1 | | 4/2001 | Koenig et al. |
| 6,361,514 | B1 | * | 3/2002 | Brown et al. ............ 602/23 |
| 6,464,659 | B1 | * | 10/2002 | DeToro et al. ............ 602/27 |
| 6,523,201 | B1 | * | 2/2003 | De Michele ............ 5/648 |
| 7,418,755 | B2 | | 9/2008 | Bledsoe et al. |
| D660,971 | S | * | 5/2012 | Franke et al. ............ D24/192 |
| 8,230,619 | B2 | * | 7/2012 | Salvatelli et al. ............ 36/88 |
| 2003/0196352 | A1 | | 10/2003 | Bledsoe et al. |
| 2004/0031169 | A1 | | 2/2004 | Jensen et al. |
| 2004/0103561 | A1 | | 6/2004 | Campbell et al. |
| 2004/0194352 | A1 | | 10/2004 | Campbell et al. |
| 2008/0269656 | A1 | | 10/2008 | Arnold et al. |
| 2009/0133292 | A1 | * | 5/2009 | Salvatelli et al. ............ 36/110 |

* cited by examiner

*Primary Examiner* — Jila M Mohandesi
(74) *Attorney, Agent, or Firm* — David F. Jacobs; Smith & Hopen, P.A.

(57) ABSTRACT

A shoe and boot, particularly for post-surgery, diabetic, or post-trauma use. It is intended to be worn by a patient who has a wound located on the forefoot and midfoot regions of the foot. An upper assembly and a lower assembly including a raised platform and a base platform. The raised platform has less longitudinal extent than the base platform. A gap is formed when a foot rests primarily upon the raised platform between the base platform and the bottom of the foot. A removable soft, cushioning insert may be placed into the gap. The inset can vary in height and density in order to provide optimum comfort throughout the various stages of the healing process.

10 Claims, 6 Drawing Sheets

ORTHOPEDIC SHOE/BOOT FOR USE WITH FOOT WOUNDS AND FOR POST OP AMBULATION

BACKGROUND OF THE INVENTION

1. Field of the Invention

This invention relates generally to the field of orthopedic devices. More specifically, it relates to an orthopedic device allowing support for assisting in the stabilization and proper healing of ulcerative or pre-ulcerative conditions, post-operative off-loading of forefoot, wounds on the foot, or other conditions of the foot, especially for diabetic patients.

2. Brief Description of the Related Art

The human foot contains more than 26 bones, 33 joints, and more than a hundred muscle, tendons and ligaments. A foot is generally split up into three separate areas; hindfoot, midfoot, and forefoot. The hindfoot contains the talus (or ankle bone) and the calcaneus (or heal bone). Midfoot consists of five bones; the cuboid, navicular, and three cuneiform bones. Together the bones of the midfoot form the arches of the foot. Finally, the forefoot is composed of five toes and the corresponding five proximal long bones forming the metatarsus. Four of the toes are comprised of three phalange bones and the fifth toe (the big toe) has two phalange bones.

Wounds to the foot can be somewhat common injuries. Wounds can either be internal or external and can be caused by varying factors. For example, external wounds can be produced from external trauma, lacerations or burns. Some of these wounds can be deliberate, such as an incision for surgery. Other wounds can be unintentional, such as cuts. Finally, there are wounds caused by friction/pressure, such as foot ulcers. In fact, excessive pressure is a leading cause of ulcers in diabetic patients.

Every type of wound has the potential to cause additional complications to the affected foot. One major complication that physicians commonly have to address is infection. There are many different types of foot infections that vary in levels of complexity. To prevent injuries from getting worse, it is essential that physicians and patients have access to areas where a wound exists in order to properly care and treat the foot. It is also imperative that the area where the foot is wounded does not receive additional force that may aggravate existing issues or cause new problems.

Patients with diabetes are faced with especially difficult challenges when it comes to foot wounds. One such problem is called neuropathy or polyneuropathy, which is damage to the nerves caused by high blood sugar levels. Individuals with neuropathy or polyneuropathy suffer from a loss of feeling in the plantar surface, or bottom of the foot, which may extend from the toes up the foot to the heel and eventually up the leg. Because of this loss of protective sensation, a sense of when something is harmful to the foot, diabetic patients are especially susceptible for developing pressure ulcers.

Diabetes may also lead to many different vascular diseases, such as peripheral arterial disease (PAD). PAD occurs when narrowed arteries reduce blood flow to limbs. This reduced blood flow results in extremities, usually feet and legs, receiving insufficient blood flow to function properly. Symptoms include painful cramping after activities, such as climbing stairs, leg numbness or weakness, and sores on toes and feet that don't heal.

Diabetes patients experience varying degrees of vascular diseases and neuropathy. 60-70% of diabetics have mild to severe forms of nerve damage. In extreme cases, patients have little to no feeling in their feet. Lack of sensitivity combined with increased pressure and poor circulation often cause wounds to form and or increase in severity. For example, when a wound develops, patients may be unaware of the wound, resulting in the patient continuing to apply external factors that further aggravate the wounds. Further aggravation of the wound can potentially lead to additional tissue damage, ulcers, even infection, and often amputation. The most common complication leading to hospitalization in diabetic patients is foot ulcers.

Diabetes affects approximately 8.3% of people in the United States (about 26 million people), including approximately 7 million undiagnosed people. In 2010, 1.9 million new cases of diabetes were diagnosed in individuals twenty years of age and older. It is estimated that diabetes affects 250 million people worldwide. 1 in 4 patients with diabetes develop foot ulcers with over 50% requiring hospitalization.

Once infection sets in, amputation may be the only option for the patient's survival. Over 80% of lower limb, non-traumatic amputations occur in patients with diabetes. Approximately 1 in 5 foot ulcers will require amputation. Every year more than 82,000 amputations are performed on diabetics in the United States. Worldwide someone loses a limb to diabetes every 20 seconds. For diabetic patients the 5 year mortality rate after a limb amputation is 68%, second only to lung cancer. According to the Centers for Disease Control and Prevention, diabetes contributed to a total of 231,404 deaths in 2007.

Diabetes has national economic detriments, in addition to the physical complications. The Centers for Disease Control and Prevention estimated the total direct medical costs to be $116 billion in 2007. Indirect costs were estimated to be $58 billion in 2007. These staggering numbers necessitate the creation of ways to reduce, heal and prevent foot wounds, both in diabetic patients and in the general population.

Currently, there are several different types of shoes (for example, U.S. application number 20040031169, published 2004 and U.S. Pat. No. 5,566,479, granted 1996), boots (for example, U.S. Pat. No. 5,078,128, granted 1992, 5,329,705, granted July 1994, U.S. Pat. No. 5,378,223, granted January 1995, U.S. Pat. No. 5,464,385, granted November 1995, and 5,761,834, granted June 1998), and orthotic inserts (for example, U.S. App. No. 20040103561, published June 2004 and U.S. App. No. 20040194352) that attempt to reduce foot wound injuries, heal existing wounds and prevent future injury. While each specific embodiment has its own advantages and disadvantages, they all share common disadvantages. One such disadvantage is that there are still times when pressure and/or friction are applied to the wound site. Each embodiment also requires a patient to physically remove the device in order to gain access to the wound site. Finally, each embodiment generally lacks adaptability to change as the wound site changes. There are also significant stability issues with prior art designs.

Another widely established method, called the total contact cast (TCC), has widely been used for off-loading planter ulcers. Developed in the 1950s, the application and removal takes a number of time consuming steps. A patient must endure two applications, inner and outer, of plaster. Once the plaster is applied the patient has to wait for up to a 24-hour period before they can apply any weight to the TCC. Removal of the cast is also a time consuming process that must occur at least once a week. While the TCC is applied, the patient and the physician do not have access to the wound site. Additionally, the TCC cannot adapt to the changing circumstances of the wound without going through the tedious removal and application of the cast. Finally, the cast has the potential to cause additional ulcers or wounds in new locations because of its inability to adjust the pressure applied to the foot and leg.

Shoes, such as the DARCO® Ortho-Wedge, promote healing by shifting the weight from the forefoot to the midfoot and heel. Generally used with VELCRO®, these shoes allow for easy removal and application but still lack the ability for easy access while the shoe is on. Another disadvantage associated with these shoes is that they can't adapt as the wound adapts. In addition, the shoes can be highly unstable for patients with reduced sensitivity in their feet, such as diabetic patients. This lack of stability can cause a patient to fall, trip or otherwise put themselves at greater risk to receive additional injuries or wounds.

The prior art lacks a device that offloads the pressure from a patient's forefoot, but maintains stability while in use. Prior art also lacks adaptability as the wound changes. Finally, there is a need for a shoe that allows access to the affected area while in use.

However, in view of the art considered as a whole at the time the present invention was made, it was not obvious to those of ordinary skill in the field of this invention how the shortcomings of the prior art could be overcome.

BRIEF SUMMARY OF THE INVENTION

The long-standing but heretofore unfulfilled need for a shoe and boot that reduces pressure and friction on the forefront of the foot is now met by a new, useful, and nonobvious invention.

The novel structure of the shoe includes an upper assembly, conventionally known as the "upper" secured to a sole assembly. The upper is adapted to surround the heel, sides, and dorsal portions of the foot. An open region of the upper is located in the toe region. A forward portion of the upper on the dorsal of the foot is divided into an inner and an outer flap. There is a strapping means interconnecting the outer flap portion with the inner flap portion in order to secure the flaps to the dorsal region of the foot The sole assembly comprises two separate platforms: a base platform and a raised platform. The base platform extends from the hindfoot to the forefoot. In contrast the raised platform extends hindfoot into the midfoot. A gap is created from the height differential between the raised platform and the base platform. An insert comprised of soft, cushioning material, such as foam, can be placed into the gap area of the shoe. The insert can be either permanent or temporary and varies in density and height depending on the patient's needs and tolerance level. A foot rests primarily upon the raised platform with limited to no weight applied to the insert.

The novel structure of the boot includes an upper assembly, conventionally known as the "upper" secured to a sole assembly. For the boot, an upper consists of two separate portions: a top portion and a bottom portion. The bottom portion is comprised the same as the upper in the shoe, except it extends from the heel into the top portion. Top portion comprises two flaps, an inner flap and an outer flap, that are adapted in length to surround the leg. A strap means interconnecting the outer face portions secures the flaps to the leg. The structure of the sole is built the same for the boot as it is for the shoe.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiment, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

The present invention is directed to a shoe, and more specifically, a shoe designed to take pressure off wound sites for patients, especially diabetic and post-operative patients. The preferred embodiments of the shoe are designed to remove forces on the forefoot and midfoot regions by applying more force to the hindfoot regions. The preferred embodiments of the present invention are further designed to reduce the amount of friction caused to the plantar surface of the foot. In addition, the preferred embodiments of the present invention are designed to increase stability for the wearer of the shoe; especially in view of prior art FIG. 1.

Figure 1:
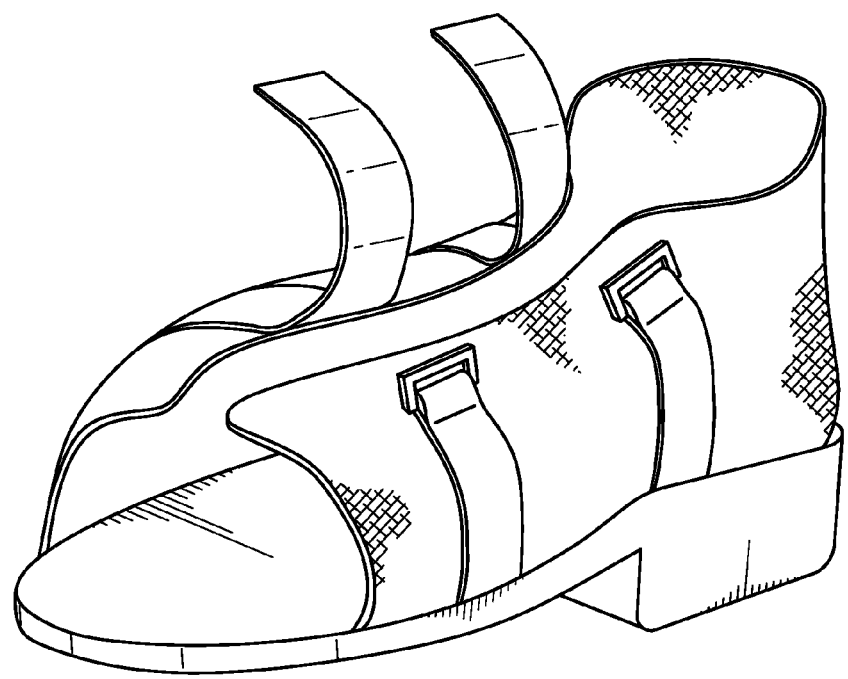
FIG. 1 depicts the prior art.

FIG. 1 depicts the prior art as disclosed in U.S. Pat. No. 4,677,767, issued July 1987 and U.S. Pat. No. 5,138,777, issued August 1992. Specifically, the prior art illustrated in FIG. 1 depicts an embodiment of the DARCO® ORTHO WEDGE, herein incorporated by reference.

Figure 2:
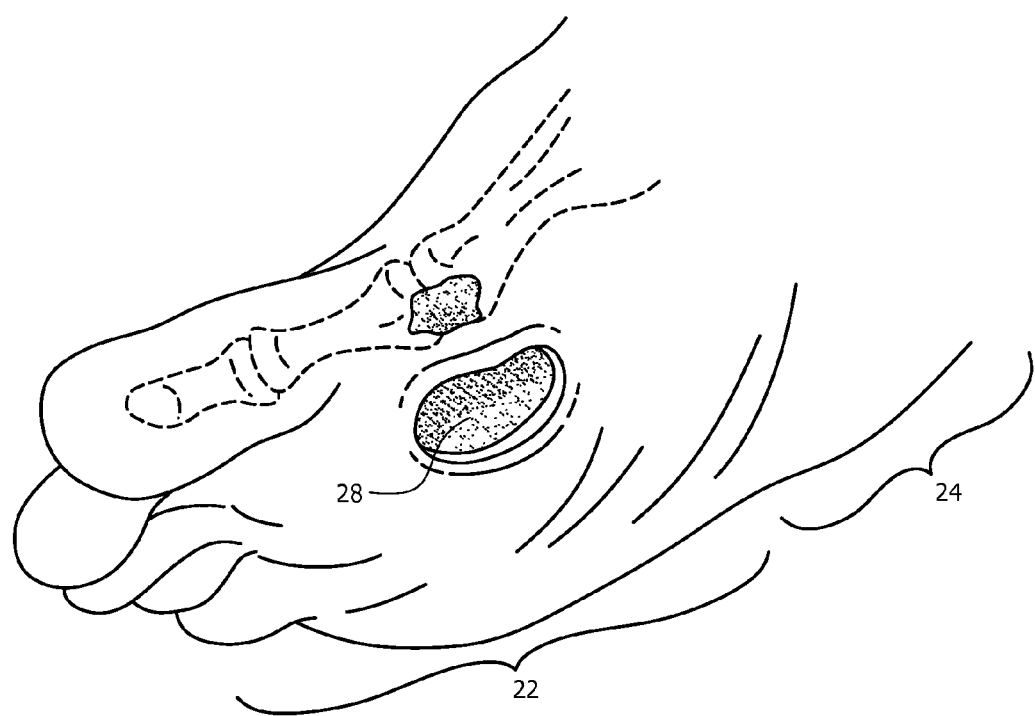
FIG. 2 depicts a foot with an ulcer located on the forefoot.

FIG. 2 depicts a general view of a foot 20 divided into the forefoot 22 and midfoot 24 regions. An ulcer 28 is depicted on the forefoot 22, a common area for ulcers to appear. While this particular figure illustrates an ulcer it can be seen to encompass various wounds associated with the plantar or bottom of the foot.

Referring to FIGS. 3-6, which illustrate a series of two preferred embodiments of the invention, the post-operative shoe is indicated generally at 10, with an upper assembly 2 similar to prior art upper assembly, see FIG. 1. The difference between the prior art and the present invention resides in the sole assembly indicated generally at 4. The sole assembly consists of an elevated platform 6, which the hindfoot 26, i.e. heal, rests on that can extend outwards through the midfoot 24. Elevated platform 6 is fixedly mounted to the lower sole 8 or integrally formed with the lower sole 8. The lower sole 8 and elevated platform may be comprised of an inner sole 14 and an outer sole 16. With the outer sole 16 comprising wear-resistant material, such as rubber or plastic material, and containing a non-slip tread or crepe pattern.

Figure 4:
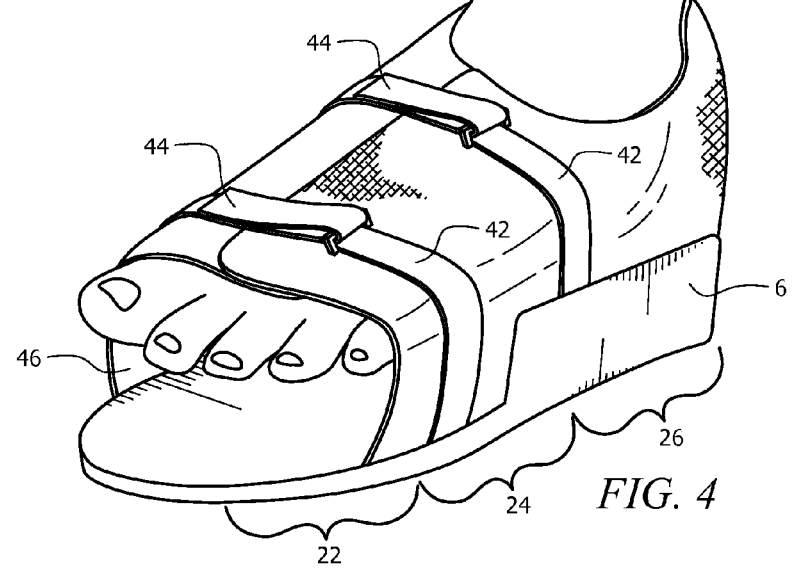
FIG. 4 depicts an ulcerated foot inside the shoe without foam padding.
Figure 5:
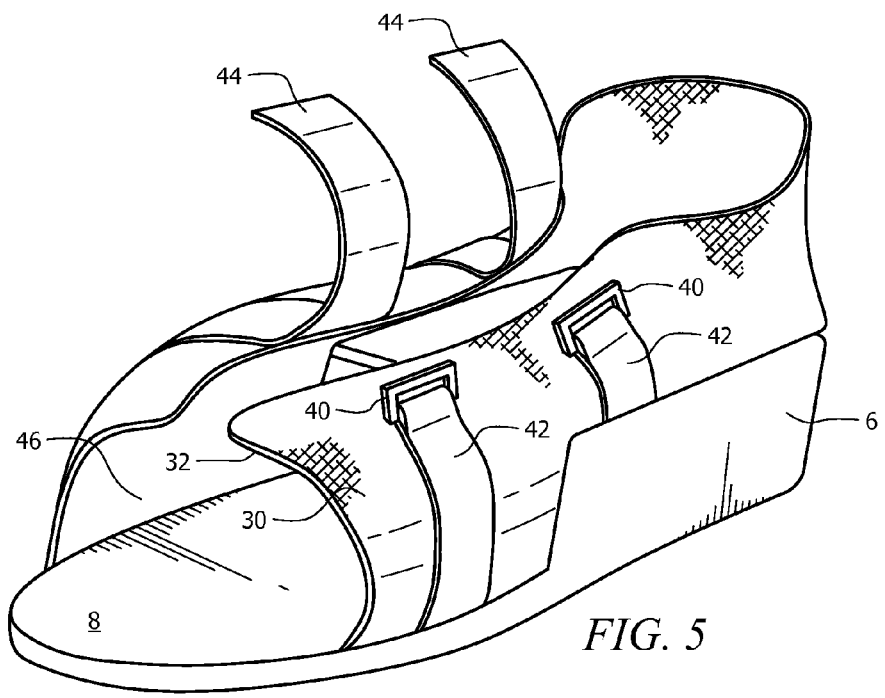
FIG. 5 depicts a side view of the shoe.

The elevated platform 6 can extend varying degrees in length to encompass more or less of the foot. FIG. 4 and FIG. 5 depict a preferred embodiment of the invention where the wedge extends from the hindfoot 26 into the midfoot 24. While in this position the forefoot 22 is not engaged with the sole of the shoe, thus hanging freely. The gap between where the foot hangs freely and the sole of the shoe is called the "open" portion of the shoe, generally indicated as 46. This allows the treating physician access to the ulcer 28, or other wound, while the patient is being treated. It also allows little-no pressure and/or friction to be applied to the wounded portion of the foot. In another embodiment the elevated wedge can be primarily located under the midfoot 24, leaving the forefoot 22 and the hindfoot 26 hanging freely.

Figure 3:
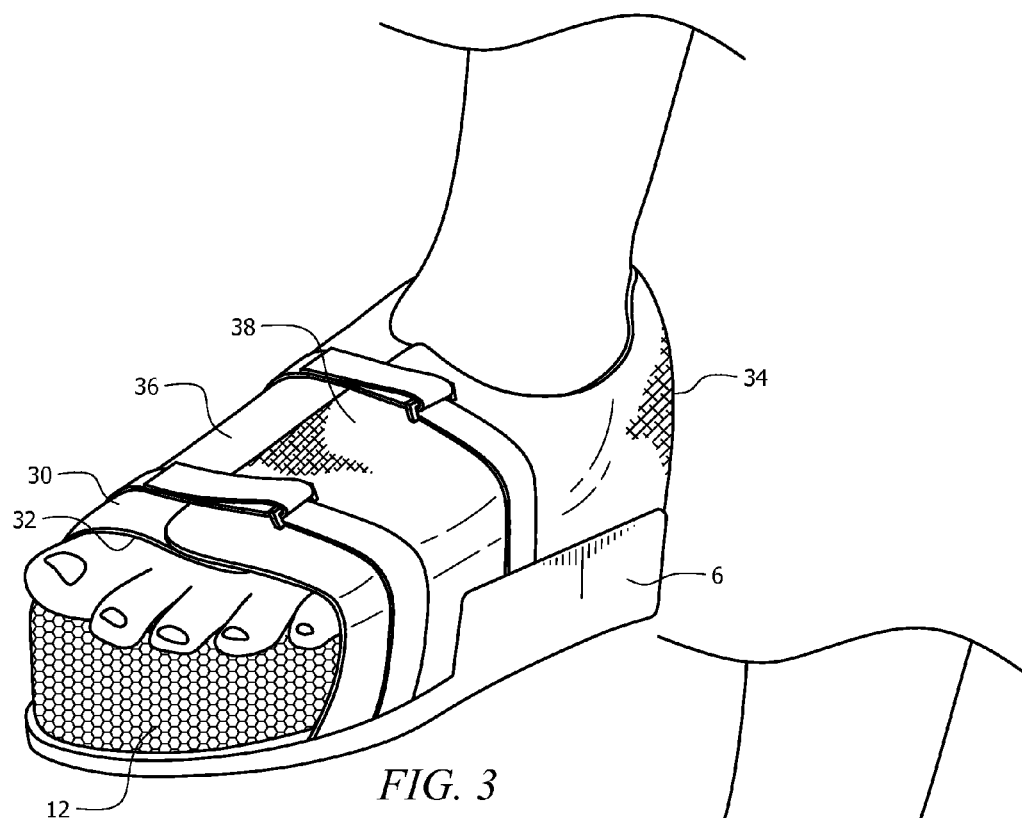
FIG. 3 depicts an ulcerated foot inside the shoe with foam padding.
Figure 6:
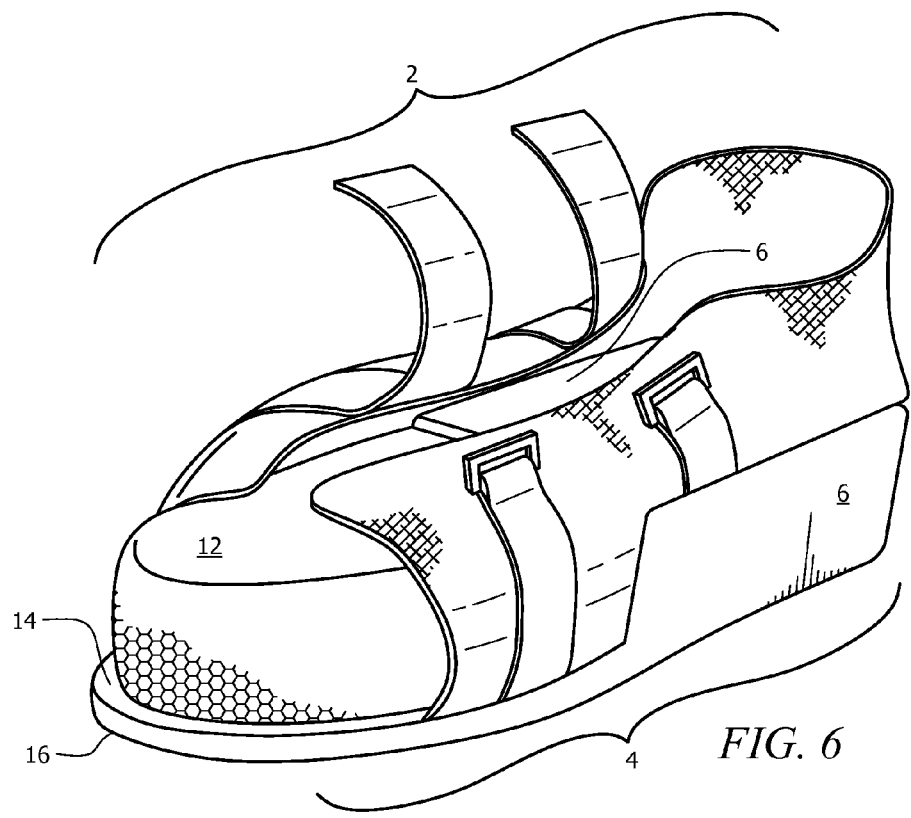
FIG. 6 depicts a side view of the shoe with foam insert.

FIG. 3 and FIG. 6 depict another preferred embodiment of the invention. An insert 12, comprising soft, cushioning material, such as foam, can be inserted into the open portion of the shoe 46. It is possible for the foam to be a single, permanently attached insert. In order to achieve this, the foam insert is permanently attached to the sole of the shoe using conventional means.

In a preferred embodiment foam insert 12 can be removable, wherein the shoe can move between FIGS. 3 and 4 by the removal and addition of insert 12 into open space 46. While insert 12 can be placed into open space 46 loosely, it can also be fixedly placed. Fixed placement occurs from the insert engaging the lower sole through an attachment means, such as through the use of VELCRO®. The insert can vary in height and density levels to provide differing degrees of support and comfort throughout the healing process.

Figure 7:
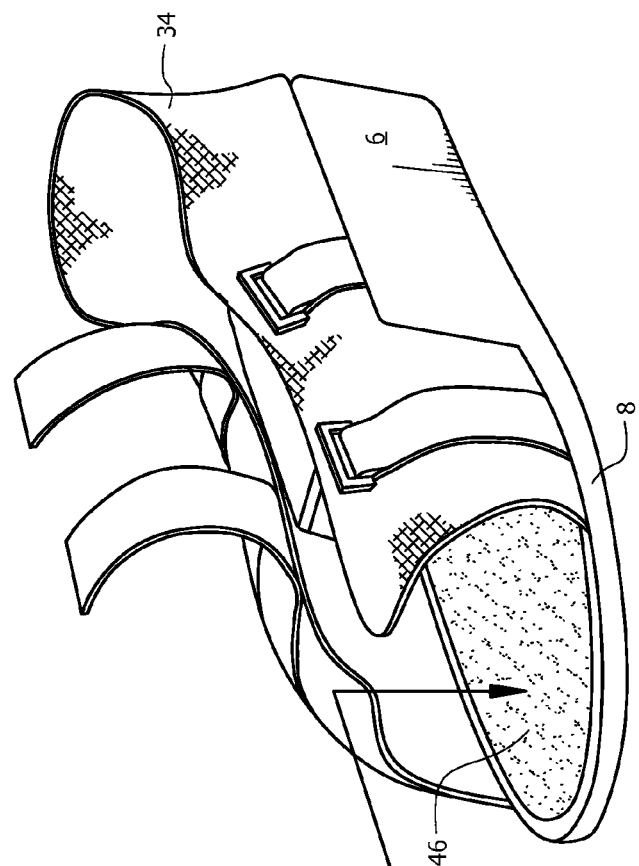
FIG. 7 depicts an alternative embodiment of the shoe with multiple foam insert replacements.
Figure 7:
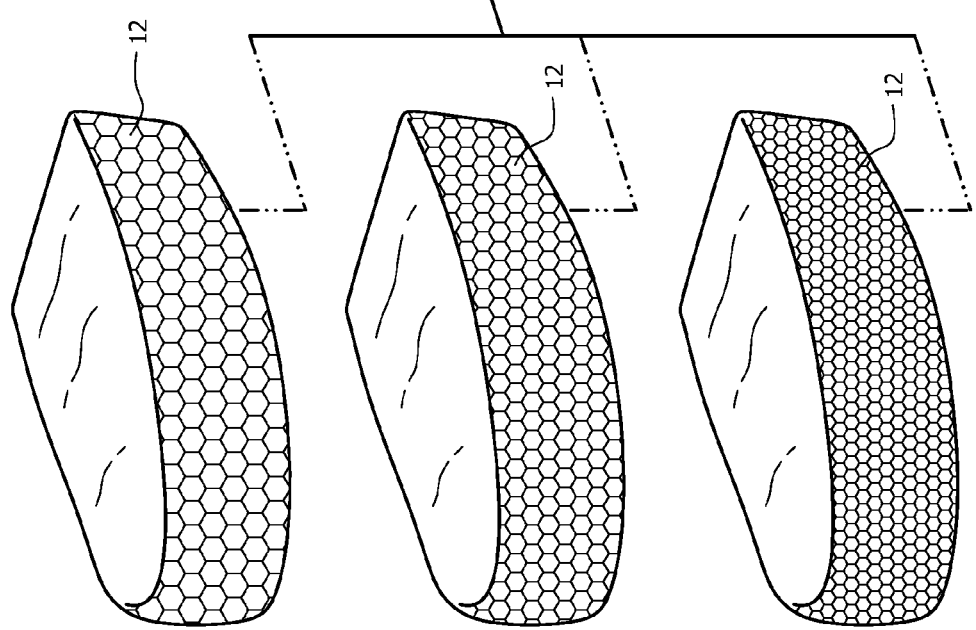
Figure 8:
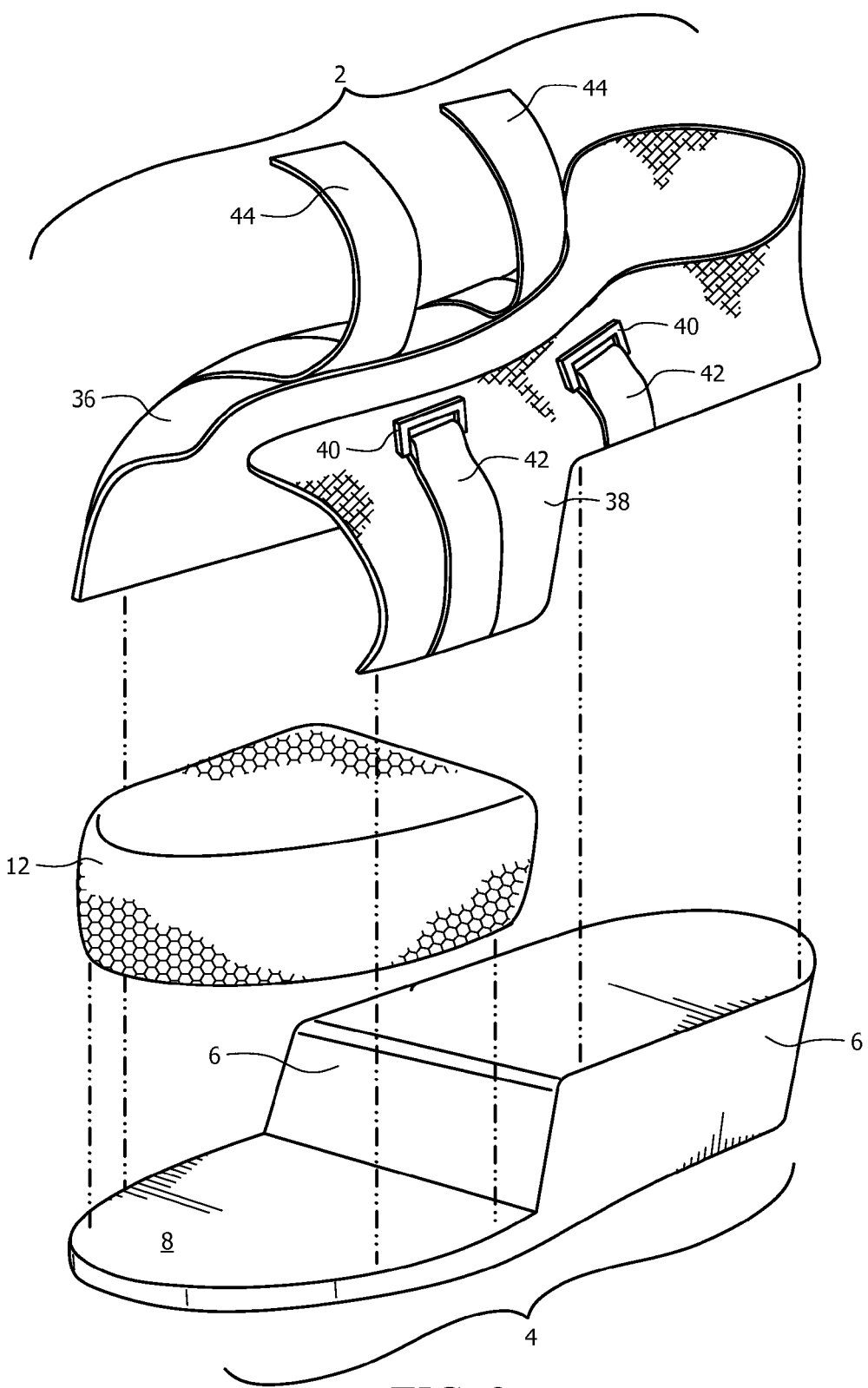
FIG. 8 depicts an exploded view of the shoe.

FIG. 7 illustrates inserts 12, from low to high density which can be inserted into open space 46 throughout the life of the shoe. As an alternative to foam inserts, gel, heating and cooling pads, medicated pads etc. can be inserted into open space 46.

An upper assembly, known conventionally as "the upper" is secured to lower sole 8 portion of the shoe by conventional techniques, preferably by adhesive bonding. Similar to the construction of the upper in U.S. Pat. No. 5,138,777, U.S. Pat. Nos. 5,940,992, and 4,677,767, herein incorporated by reference, upper assembly 2 comprises outer wall 30 and inner wall 31. Outer 30 usually consists of materials such as nylon mesh, vinyl, leather or other suitable materials. In contrast, inner layer 31 comprises a lining of soft comfortable material such as foam. Inner layer is often laminated between two layers of outer wall 30. Heal 34 may also be incorporated into the upper design as mentioned in U.S. Pat. No. 5,940,992. Upper 2 extends the full length of the shoe attached along the sides of the shoe in the direction of the shoe tip. An open area for the toe region is left in upper 2 as shown in FIG. 3.

A forward portion of upper 2 assembly is formed with inner foot flap 36 and outer foot flap 38. Outer foot flap 38 has two rings 40 on the surface wherein each ring is retained by straps of flexible non-elastic material 42. The two rings 40 are located along a straight line axis from each other moving from forefoot 22 region towards hindfoot 26 region. One ring 40 is located closer to forefoot 22 region and the other ring 40 is located towards the midfoot 24/hindfoot 26 region. Closure strap 44 is provided for each ring 40. Each closure strap 44 consists of two ends. A first end attaches to the sole of the shoe through conventional means. A second end of closure strap 44 is threaded through its corresponding ring 40. After closure strap 44 has been threaded through ring 40, the end portion is folded over ring 40, wherein it engages with the rest of the closure strap through an attachment means, such as VELCRO®. Closure straps 44 can be varying lengths, but the strap towards forefoot 22 will generally be smaller compared to the length of closure strap 44 closer to hindfoot 26.

Another embodiment of upper 2 can be seen in U.S. Pat. No. 4,677,767 and U.S. Pat. No. 5,138,777. Here the forward portion of the upper assembly is formed with a left and right flap. The left flap is longer than the right flap and folded under the right flap. In conformance with U.S. Pat. No. 5,138,777, each flap contains a closure strap that engages the corresponding rings similar to what has been described above. Additional means of securing the foot through use of an upper exists, such as the one disclosed in U.S. Pat. No. 6,212,798, herein incorporated by reference.

Figure 9:
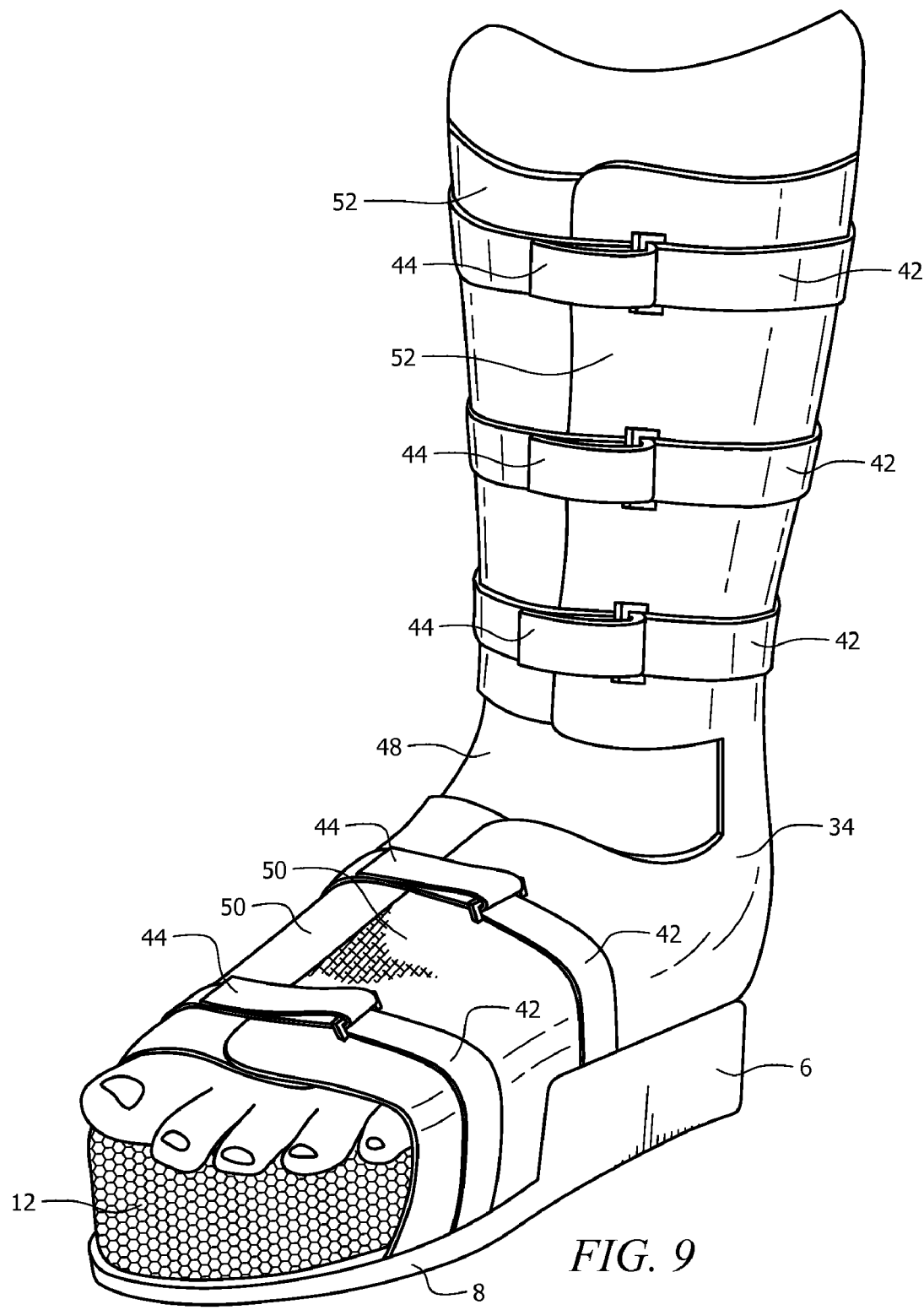
FIG. 9 depicts an alternative embodiment where the shoe is in the form of a boot with a foam insert.

FIG. 9 depicts a preferred embodiment of the invention wherein the invention is in the form of a boot. In this embodiment heal 34 portion of the upper extends up the leg towards the knee. Two additional, larger flaps 52, an inner and an outer, wrap around the leg securing the flaps to the leg using the same method described for securing lower flaps 50 to the foot. Open space 48 can be formed in the upper on the dorsal side of the foot where the foot naturally bends for comfort. In another embodiment, the upper of the boot may consist of a walking shell with upwardly turned edges along the sides and heal areas to provide additional support, such as that seen in U.S. Pub. No. 2003/0196352.

It is foreseeable that a hard, protective shell be placed on the outer portions of the shoe and boot. Examples of the use of a protective outer shell can be shown in AIRCAST® walking braces. A hard plastic shell is placed on the outside of the upper to protect the foot and leg.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

GLOSSARY OF CLAIM TERMS

Dorsal: Refers to the back or upper surface of a body part. Dorsal portions of foot, generally refers to the top of the foot, or the area of the foot not facing the ground when standing or walking.

Foot: Lower extremity of the vertebrate leg below the ankle, that is in direct contact with the ground during standing or walking. Generally split up into three separate areas; hindfoot, midfoot, and forefoot Heel: the posterior end of the foot below the ankle.

Longitudinal Extent: The length of the object.

Sole: the under surface of a shoe or boot.

Upper Assembly: Assembly above the sole or bottom portion of a shoe.

Wound: A type of injury in which the skin is torn, cut, or punctured (known as an open wound) or where blunt force trauma causes a contusion (known as a closed wound).

What is claimed is:

1. A shoe for use in evaluating and supporting wound, postop and fracture recovery to a patient's foot, comprising:
   an upper assembly secured to a sole assembly;
   said upper assembly adapted to surround the heel, sides and dorsal portions of a foot;
   said upper assembly having an open toe region allowing access to bottom forefoot region of said foot; and
   said sole assembly comprising a raised platform and a base platform;
   wherein said base platform extends from the heel to the toes;
   said base platform being flat;
   said raised platform having a longitudinal extent extending from said heel to a midfoot region of said foot;
   said raised platform being a permanent fixture of said shoe;

said base platform extending from a lower part of said raised platform, forming a gap between the top of the raised platform and the top of the base platform;

said gap extending longitudinally, such that forefoot region of said foot substantially hangs freely over said base platform;

a removable soft, cushioning insert with an attachment mechanism for attaching said removable soft, cushioning insert into said gap with said sole assembly, wherein said removable soft insert has a sliding abutting engagement with said raised platform;

said removable soft, cushioning insert extending from said midfoot to said toes;

the sole assembly, wherein said sole assembly is substantially flat.

2. The shoe as in claim 1, wherein said insert consists of materials selected from the group consisting of foam and gel.

3. The shoe as in claim 1, wherein said insert varies in degrees of density and height.

4. The shoe as in claim 1, wherein said upper assembly is further comprising;
an inner wall and an outer wall,
said outer wall formed of material selected from the group consisting of nylon mesh, vinyl, and leather
said inner wall formed of foam.

5. The shoe as in claim 1, said sole assembly further comprising an inner sole and an outer sole, further comprising:
said outer sole formed of a wear-resistant material.

6. A boot for use in evaluating and supporting wound, postop and fracture recovery to a patient's foot, comprising:
an upper assembly secured to a sole assembly;
said upper assembly having a top portion and a bottom portion;
said bottom portion of said upper assembly adapted to surround the heel, sides and dorsal portions of the foot; and
said bottom portion having an open toe region allowing access to bottom forefoot region of said foot;
said top portion of said upper assembly extending from the heel towards the knee;
said top portion adapted to surround the leg;
wherein said top portion of said upper assembly is attached to said bottom portion;
said sole assembly comprising a raised platform and a base platform;
wherein said base platform extends from the heel towards the toe;
said base platform being flat;
said raised platform having a longitudinal extent extending from said heel to a midfoot region of said foot;
said raised platform being a permanent fixture of said shoe;
said base platform extending from the lower part of said raised platform, forming a gap between the top of the raised platform and the top of the base platform;
said gap extending longitudinally, such that forefoot region of said foot substantially hangs freely over said base platform;
a removable soft, cushioning insert with an attachment mechanism for attaching said removable soft, cushioning insert into said gap with said sole assembly, wherein said removable soft insert has a sliding abutting engagement with said raised platform;
said removable soft, cushioning insert extending from said midfoot to said toes;
the sole assembly, wherein said sole assembly is substantially flat.

7. The boot as in claim 6, wherein said insert consists of materials selected from the group consisting of foam and gel.

8. The boot as in claim 6, wherein said insert varies in degrees of density and height.

9. The boot as in claim 6, further comprising;
an inner wall and an outer wall,
said outer wall formed of material selected from the group consisting of nylon mesh, vinyl, and leather
said inner wall formed of foam.

10. The boot as in claim 6, said sole assembly further comprising an inner sole and an outer sole, further comprising:
said outer sole formed of a wear-resistant material.

* * * * *